(12) United States Patent
Dovlatabadi

(10) Patent No.: US 10,905,729 B1
(45) Date of Patent: Feb. 2, 2021

(54) FORMULATIONS AND METHODS FOR WOUND TREATMENT

(71) Applicant: Sorush, LLC, Birmingham, AL (US)

(72) Inventor: Hossein Dovlatabadi, Birmingham, AL (US)

( * ) Notice: Subject to any disclaimer, the term of this patent is extended or adjusted under 35 U.S.C. 154(b) by 350 days.

(21) Appl. No.: 15/976,748

(22) Filed: May 10, 2018

Related U.S. Application Data

(63) Continuation-in-part of application No. 13/212,918, filed on Aug. 18, 2011, now abandoned.

(51) Int. Cl.
*A61K 9/00* (2006.01)
*A61K 36/185* (2006.01)
*A61P 17/02* (2006.01)

(52) U.S. Cl.
CPC .......... *A61K 36/185* (2013.01); *A61K 9/0014* (2013.01); *A61P 17/02* (2018.01); *A61K 2236/331* (2013.01); *A61K 2236/333* (2013.01)

(58) Field of Classification Search
CPC ...... A61K 9/00; A61K 9/0012; A61K 9/0014; A61K 9/70; A61K 9/7007; A61K 9/7015
See application file for complete search history.

(56) References Cited

U.S. PATENT DOCUMENTS 8,268,368 B2 * 9/2012 Reddy .................. A61K 36/889
424/727

OTHER PUBLICATIONS

Carlson et al (Topical Antibiotic Dosage Forms, Secundum Artem, Current & Practical Information for the Compounding Pharmacist, vol. 1, No. 2 Jul. 1988) (Year: 1988).*
F Malekzadeh, Antimicrobial Activity of Lawsonia inermis L, Applied Microbiology, Apr. 1968, pp. 663-664, vol. 16, No. 4. (Year: 1968).*

* cited by examiner

*Primary Examiner* — Micah Paul Young
(74) *Attorney, Agent, or Firm* — Lanier Ford Shaver & Payne; Gerald M. Walsh

(57) ABSTRACT

An aqueous extract of *Lawsonia inermis* comprising forming an extraction from 1% to 20% of dried *Lawsonia inermis* leaves with water. The antibiotics polymyxin B, clindamycin, and gentamycin are each added to the water before or after extraction in the amount of 0.001% to 0.003%. After forming the aqueous extract of *Lawsonia inermis*, it has no antibiotic activity and the antibiotics are not detectable by chemical analysis. The aqueous extract of *Lawsonia inermis* is stable for at least 28 days for the topical treatment of wounds and has been stable up to two years in clinical testing. The aqueous extract of *Lawsonia inermis* extract is applied with a spray to the surface of the wound, followed by the application of an extract-soaked gauze dressing to the surface of the wound. The extract is effective on various types of wounds and also in healing wounds in patients who are not healing with traditional therapies.

14 Claims, 10 Drawing Sheets

Table 2

| Patient Identifier | Wound type | Initial Size in Cm. | Final Size in Cm. | Beginning of treatment | End of Treatment | Size difference in percentage | Day's Followed |
|---|---|---|---|---|---|---|---|
| GG | Dehiscence | 1.5x1 | Healed | 2/13/11 | 2/21/11 | 100 | 11 |
| DC | Dehiscence | 7x2.3x3 | Healed | 12/18/09 | 1/16/10 | 100 | 30 |
| SM | Dehiscence | 10.5x4x4 | Healed | 12/30/09 | 2/8/10 | 100 | 40 |
| EH | Dehiscence | 5.5x2x1 | Healed | 1/11/10 | 1/25/10 | 100 | 14 |
| RQ | Dehiscence | 5x3x1 | 3.7x.8/.5 | 8/25/10 | 9/22/10 | 90.1 | 28 |
| BC | Dehiscence | 11x3x2 | 7x1x.5 | 10/18/10 | 11/22/10 | 94.7 | 42 |
| MV | Dehiscence | 8x2.5x1.5 | 7x1.5 | 12/14/10 | 1/3/11 | 65 | 20 |
| MM | Dehiscence | 9x3x1 | 9x.22x.4 | 6/28/11 | 7/14/11 | 70.67 | 16 |
| DP | Infection | 6x1.8x.5 | 2.8x.5 | 12/29/09 | 2/8/10 | 84.3 | 41 |
| SL | Infection | 4.5x2.5 | 3x.5 | 9/2/12 | 9/19/12 | 87 | 17 |
| JB | Wagner 1 | 1.2 | Healed | 9/9/09 | 9/14/09 | 100 | 5 |
| JM | Wagner 2 | 6.7x2.5x2.5 | 6x2x.4 | 4/20/11 | 5/9/11 | 88 | 27 |
| EC | Wagner 2 | 9x2x2.3 | 7.5x.8x1.2 | 11/14/11 | 11/28/11 | 82.6 | 14 |
| BS | Wagner 3 | 5.5x1x3 | 4x.8 | 9/28/09 | 11/2/09 | 80.6 | 37 |
| LT | Wagner 3 | 2x2x5 | 3x1.5 | 3/8/10 | 3/22/10 | 77.5 | 15 |
| TG | Wagner 3 | 8x3.5x5 | 4.5x2x2.4 | 3/25/10 | 4/26/10 | 84.6 | 32 |
| RH | Wagner 3 | 7x4.5x2.5 | 5x2 | 5/3/10 | 7/6/10 | 87.3 | 63 |
| RH | Wagner 3 | 7x4.2x2.5 | 5x2.5 | 5/3/10 | 7/6/10 | 84.12 | 64 |
| VM | Wagner 3 | 2x1.5x2 | 1.5x.5x.5 | 5/7/10 | 6/7/10 | 93.75 | 31 |

FIG. 3

FORMULATIONS AND METHODS FOR WOUND TREATMENT

CROSS-REFERENCE TO RELATED APPLICATIONS

This application is a continuation-in-part of U.S. patent application Ser. No. 13/212,918 filed Aug. 18, 2011, which is incorporated by reference herein.

FIELD OF THE INVENTION

The present application relates to stable aqueous formulations of *Lawsonia inermis* and to methods for treating wounds, including chronic wounds, using sprays or gels of the aqueous formulations.

BACKGROUND OF THE INVENTION

A skin wound is defined as a breach in the continuity of any body tissue caused by a direct injury to the skin. Approximately 5-7 million Americans are afflicted with chronic skin wounds that account for billions of dollars in medical expenses each year. The incidence of chronic wounds is expected to increase dramatically due to an increased elderly population and incidence of diabetes, a disease that is accompanied by wound-healing deficiencies. Commonly used approaches to treat chronic or acute wounds are typically based on simple wound care regimens involving debridement, cleaning, and application of moist dressings. Acceleration of wound closure not only results in decreased patient suffering and cost of wound treatment but may also minimize scarring and lead to formation of a more stable closed wound.

*Lawsonia inermis* is a plant whose leaves have long been used for many medicinal purposes including as an astringent, an antihemorrhagic agent and for its cardio-inhibitory, hypotensive, and sedative effects. It has also been used as a folk remedy for amoebiasis, headache, jaundice and leprosy. Nayak et al (Phytotherapy Research 21, 827-831, 2007) demonstrated in rats that topical application of an ethanol extract of *Lawsonia inermis* for 15 days promoted wound healing activity. Wound healing activity of *Lawsonia inermis* has not been demonstrated in humans and ethanol would not be a suitable vehicle for topical application on a wound. A problem with a *Lawsonia inermis* aqueous extract is that the wound healing properties are not stable and the wound healing activity deteriorates over one to two weeks. Thus, topical aqueous extract formulations have not been commercially useful and *Lawsonia inermis* extracts are not used topically in humans to promote wound healing. What is needed is a stable aqueous topical formulation of *Lawsonia inermis*.

SUMMARY OF THE INVENTION

The needs identified above are met by the present application providing methods and formulations for wound treatment. In embodiments, topical formulations are provided. Exemplary stable topical aqueous formulations comprise about 1% to about 20% *Lawsonia inermis* extract in water, w/w or w/v, stabilized with 0.001% to 0.003% polymyxin B, 0.001% to 0.003% clindamycin, 0.001% to 0.003% gentamicin.

In embodiments, the topical formulations are formulated as a spray, and in other embodiments the formulations can further comprise carboxymethylcellulose sodium salt, formulated as a gel. Suitably, the topical formulations have a pH in the range of about pH 4.0 to about 5.5, suitably about pH 5.0.

Also provided are methods of treating a skin wound comprising applying to a wound a stable topical formulation comprising about 1% to about 20% *Lawsonia inermis* extract in water, w/w or w/v, stabilized with 0.001% to 0.003% polymyxin B, 0.001% to 0.003% clindamycin, 0.001% to 0.003% gentamicin. A spray or gel of the *Lawsonia inermis* extract is applied directly to the wound. In other embodiments, the spray or gel is applied to a wound dressing and then the dressing is applied to the wound. In embodiments, the formulation is applied to the wound at least once per day or once per week. Suitably, the methods are useful for treating chronic wounds, including decubitus ulcers, diabetic ulcers or venous stasis ulcers. The formulations are also useful for treating post-surgical wounds.

Further embodiments, features, and advantages of the embodiments, as well as the structure and operation of the various embodiments, are described in detail below with reference to accompanying drawings.

BRIEF DESCRIPTION OF THE DRAWINGS

FIG. 3 provides a table of results from human clinical study 1 showing the efficacy and duration of topical treatment of diabetic wounds with the *Lawsonia inermis* extract.

DETAILED DESCRIPTION OF THE INVENTION

Figure 1A:
FIGS. 1A-1C show the results of treatment of a foot amputation wound using an exemplary formulation of the *Lawsonia inermis* extract described herein.

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. It should be understood that use of the term "about" also includes the specifically recited amount.

Technical and scientific terms used herein have the meaning commonly understood by one of ordinary skill in the art to which the present application pertains, unless otherwise defined. Reference is made herein to various methodologies and materials known to those of skill in the art.

In embodiments, the application provides topical formulations. The topical formulations suitably comprise the following active ingredient, Lawsonia inermis extract, stabilized with polymyxin B, clindamycin, and gentamicin. The polymyxin B, clindamycin, and gentamicin are not pharmacologically active in the extract or are not detectable after formulation of the extract or both.

As used herein, a "topical formulation" refers to a composition that is administered topically to the surface of the skin. The topical formulations can be administered to any surface of the skin, including the face, arms, back, trunk, legs, chest, feet, hands, etc., as well as the inner surface of the mouth, nasal passages, tongue, vaginal walls, etc.

Polymyxin B is an antibiotic primarily used for treatment of resistant gram-negative infections. It is derived from the bacterium Bacillus polymyxa, and is a mixture of two closely related compounds, polymyxin B1 and polymyxin B2

Clindamycin is a lincosamide antibiotic, often used to treat infections with anaerobic bacteria.

Gentamicin is an aminoglycoside antibiotic, often use to treat Gram-negative organisms.

While the amounts of the various agents in the topical formulations can be varied by those of ordinary skill in the art to obtain various changes in the properties of the formulations, suitably the amounts of the agents are described below.

Unless otherwise indicated, all percentages of the agents described herein refer to weight/weight percent (w/w %) based upon the entire weight of the formulation or weight/volume (w/v %) based upon the entire weight of the formulation.

In embodiments, the formulations further comprise extracting every 1 gram of dried Lawsonia inermis leaves with about 5 ml (20% extract w/w or w/v) to 100 ml (1% extract w/w or w/v) of purified or de-ionized (DI) water. This provides a 1% to 20% Lawsonia inermis extract, preferably extracting every 1 gram of dried Lawsonia inermis leaves with 10 ml water (10% extract, w/w or w/v).

In embodiments, suitably the extraction is made with purified or deionized water. About 0.001% to about 0.003% polymyxin B, 0.001% to about 0.0030% clindamycin, and about 0.001% to about 0.003% gentamicin (w/w or w/v) are added to the water before extraction or after extraction. The aqueous Lawsonia inermis extract by itself has no antibiotic activity. The antibiotics do not have antibiotic activity alone or in combination with the Lawsonia inermis extract. The combination of antibiotics render the Lawsonia inermis extract stable for at least 28 days.

In embodiments, suitably the topical formulations comprise about 1.0% to about 20.0% Lawsonia inermis extract. More suitably, the formulations comprise about 5.0% to about 15.0% Lawsonia inermis extract, preferably 10%.

Exemplary topical formulations include, but are not limited to, a cream, a lotion, a spray, a gel, a solution, a foam, an ointment and a mask, as well as other similar topical formulations known in the art. Suitably the formulation is formulated as a spray.

In further embodiments, the formulations can be formulated as a gel. In such embodiments, the formulations comprise carboxymethylcellulose sodium salt to form the gel. Other suitable excipients to form gels are well known in the art and can be readily used in the formulations described herein.

Suitably, the formulations exhibit a pH in the range of about 4.0 to about 7.0, more suitably about 4.5 to about 6.0.

In further embodiments, the formulations can comprise various ingredients or excipients. Exemplary ingredients or excipients are well known in the art. Such ingredients include, but are not limited to, humectants, emollients, pH stabilizing agents, preservatives, chelating agents, gelling agents, thickening agents, emulsifiers, binders, buffers, carriers, anti-oxidants, etc.

Amounts of non-active agents, including those disclosed herein, are readily determinable by those of ordinary skill in the art. Generally, the amounts and ratios of the non-active agents are determined so as to provide the topical formulations with the desired consistency, stability, delivery characteristics and other properties of the formulation.

Exemplary non-active ingredients, include for example, dimethyl sulfoxide (DMSO), propylene glycol (PG), poly (ethylene glycol) 400 (400 molecular weight (MW)) (PEG 400), Transcutol, mineral oil, sterol alcohol, acetyl alcohol, Brij 21, Brij 721, emulsifying wax, monoglyceride (GMS), Isopropyl Myristate (IPM) Carbopol, Petrolatum, The topical formulations can also comprise suitable preservatives, including for example, Methylparaben, Propylparaben and Benzyl Alcohol.

As described herein, suitably the formulations described throughout are useful in the treatment of wounds. The term "wound" is used throughout to mean a breach in the continuity of skin tissue which is caused by direct injury to the skin. Skin wounds are generally characterized by several classes: punctures, incisions, including those produced by a variety of surgical procedures (post-surgical wound), excisions, lacerations, abrasions, atrophic skin or necrotic wounds and burns, including large burn areas, and chronic wounds, such as for example, various ulcers such as decubitus ulcers (bed sores or other pressure ulcers), diabetic ulcers or venous stasis ulcers, etc.

The formulations described herein may also, in additional embodiments, comprise other active agents, including for example, additional antibiotics, various proteins, including growth factors, pain suppressants, anti-fungal agents, plant or tree extracts, etc.

In further embodiments, topical formulations are provided that consist of or consist essentially of the recited components at the recited amounts.

In formulations that consist essentially of the recited ingredients, such formulations specifically exclude other active agents, as the addition of such active agents would be considered a material alteration to such formulations and is thus excluded from such formulations that consist essentially of the recited active agents at the recited amounts.

Also provided are methods of treating skin wounds of patients, including human and animal patients. Suitably, such methods comprise applying to the wound a topical formulation as described herein, for example, an aqueous extract of Lawsonia inermis leaves produced by placing every 1 gram of dried Lawsonia inermis leaves in about 5 ml to 100 ml purified or de-ionized (DI) water, preferably 10 ml, for 0.5 to 2 hours. Such methods further include adding to the aqueous extract polymyxin B, clindamycin, and gentamicin in amounts of 0.001% (10 micrograms/ml) to 0.003% (30 micrograms/ml), w/w or w/v, for each.

The formulation is sprayed directly to the wound as well as to surrounding tissue. Alternatively, the formulation is sprayed onto wound dressing and the wound dressing is then applied to the wound. As used herein, the term "wound dressing" is used to mean any suitable article for applying to and covering a wound, so as to facilitate healing. Exemplary wound dressings include for example, gauze, various fabrics, cloths, bandages, polymers, films, etc.

In further embodiments, as described herein, the formulation further comprises carboxymethylcellulose sodium salt and is formulated as a gel. Such gels can be directly applied to the wound or can be applied to a wound dressing that is then applied to the wound.

Suitable dosing schemes for applying the formulations described herein can be readily determined by those of ordinary skill in the art. In exemplary embodiments, the formulations are applied to the wound as frequently as desired, for example once every day or once every seven days, preferably once a day. The duration of the application is dependent on the condition of the wound, the severity of the wound, and the patient's response to the formulation, the patient's age, physical health, etc. Suitably the duration of application can be from about a few days, to several weeks, to months, if necessary.

As described herein, the methods are suitably used to treat patients exhibiting skin wounds that include, for example, punctures, incisions, including those produced by a variety of surgical procedures (post-surgical wound), excisions, lacerations, abrasions, atrophic skin or necrotic wounds and burns, including large burn areas, as well as chronic wounds, such as for example, various ulcers such as decubitus ulcers (bed sores or other pressure ulcers), diabetic ulcers or venous and stasis ulcers.

The inventor has surprisingly found that the formulation is stable and that the application of the formulations described herein to various wounds dramatically shortens the healing time required. For example, wounds that typically take 3-4 months to heal are healed in a period of 4-6 weeks. In addition, chronic wounds that have been unhealed for periods of 1 year, 2 years and 20 years, have been healed in approximately 5 days, 10 days and 6 months, respectively, by application of the formulations described herein. In addition, use of the formulations described herein in wound treatment generally does not produce necrotic tissue or require surgical debridement during the healing process. These results demonstrate the unexpected and superior wound healing achieved by the methods and formulations described herein.

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

EXAMPLES

Example 1

Formation of the *Lawsonia inermis* Extract 10 grams of dried *Lawsonia inermis* leaves (www.ETSY.com) were placed in a beaker and 100 ml of distilled water were added. The mixture was stirred for 2 hours at room temperature to obtain an aqueous *Lawsonia inermis* extract designated as a 10% w/w or w/v extract. In order to produce stable wound healing properties of the extract, the antibiotics polymyxin B, clindamycin, and gentamycin were added after extraction in the amount of 0.003% each (30 micrograms/nil). The *Lawsonia inermis* extract was analyzed for antibiotic activity and for the presence of the antibiotics about two weeks after formation of the extract.

A zone of inhibition test (Kirby-Bauer Test) was used to evaluate the antibiotic activity against *Pseudomonas aeruginosa* and *Staphylococcus epidermisis*. There were six types of tests on each of the bacteria: extract alone, extract plus polymyxin B, extract plus clindamycin, extract plus gentamycin, all three antibiotics combined, and all three antibiotics combined plus extract. The extracts were stored at room temperature for three weeks before testing. The results were negative for all six types of tests on both strains of bacteria. The results demonstrate that the *Lawsonia inermis* extract has no significant antibacterial activity, the combination of the antibiotics has no significant antibacterial activity, and the *Lawsonia inermis* extract combined with all three antibiotics has no significant antibacterial activity.

A chemical analysis was performed on the extract. Gentamycin and clindamycin analyses were performed on a Shimadzu-Qtrap HPLC-MS. Polymyxin B analysis was performed on a Thermo Finnigan LCQ MS. Gentamycin was not detected in the extract at a level of 15.0 nanograms/ml, clindamycin was not detected in the extract at a level of 17.2 nanograms/ml, and polymyxin B was not detected at a level of 960 nanograms/ml. The data indicate that no significant amounts of gentamycin, clindamycin, or polymyxin B are present in the extract.

Because there are no detectable antibiotics in the extract, results from these studies suggest that there may be a chemical interaction between the antibiotics and the *Lawsonia inermis* extract that cause the antibiotics to disappear from the extract. Such an interaction may account for the stabilization of wound healing properties of the *Lawsonia inermis* extract.

Example 2

Treatment of Toe Amputation

Figure 1B:
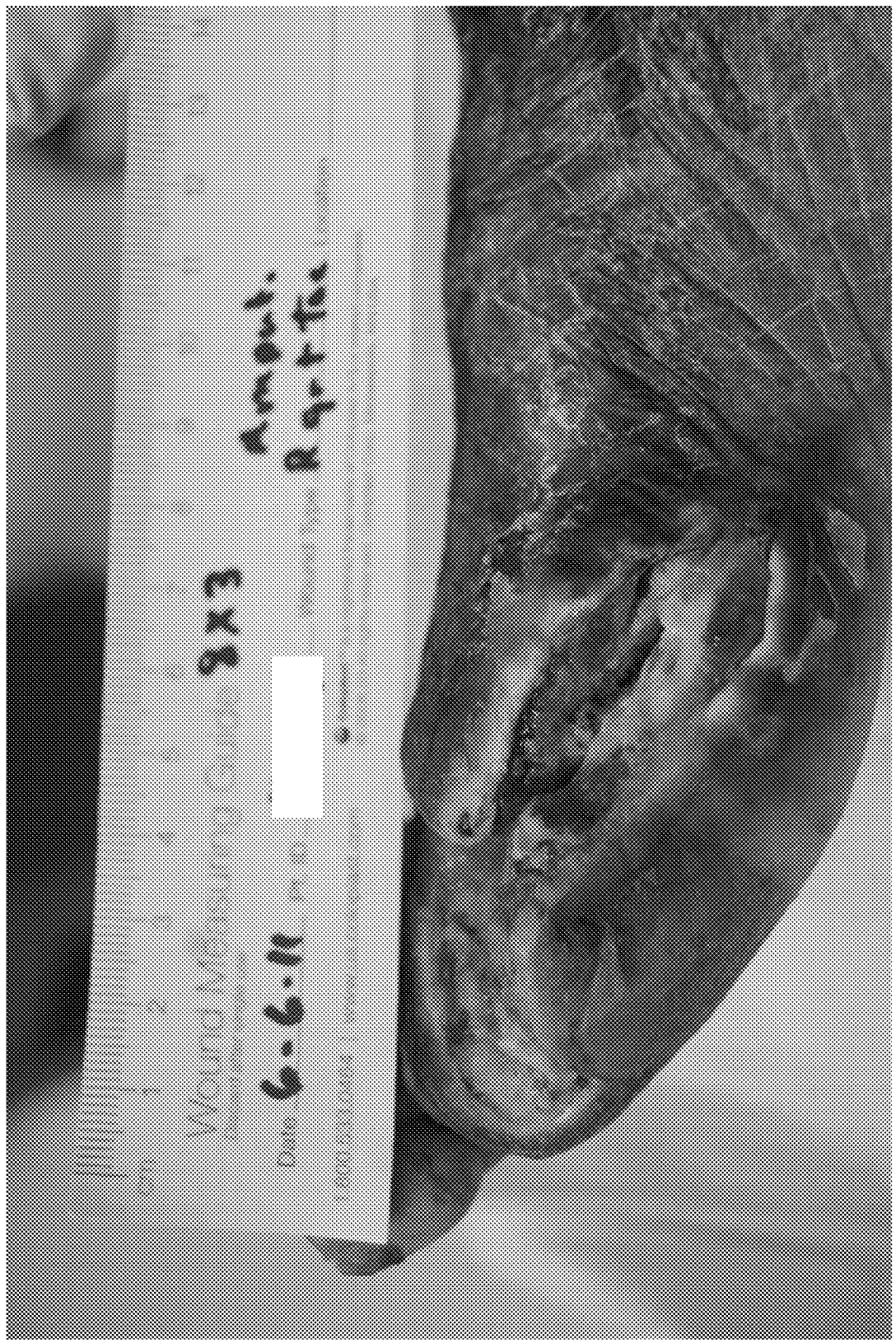
Figure 1C:

*Lawsonia inermis* extract, about 8.0% to about 13.0% w/w or w/v, was applied to a wound dressing and then the dressing was applied to the amputated toe of a 68 year-old diabetic patient. The formulation was applied to the wound once a day. FIG. 1A shows the wound at the beginning of treatment. FIG. 1B shows the wound at day 4 of treatment. FIG. 1C shows the wound at day 11 of treatment. The wound was fully healed by day 28 of treatment.

Example 3

Treatment of Hysterectomy Incision

Figure 2A:
FIGS. 2A-2F show the results of treatment of a hysterectomy wound using an exemplary formulation of the *Lawsonia inermis* extract described herein.
Figure 2B:
Figure 2C:
Figure 2D:
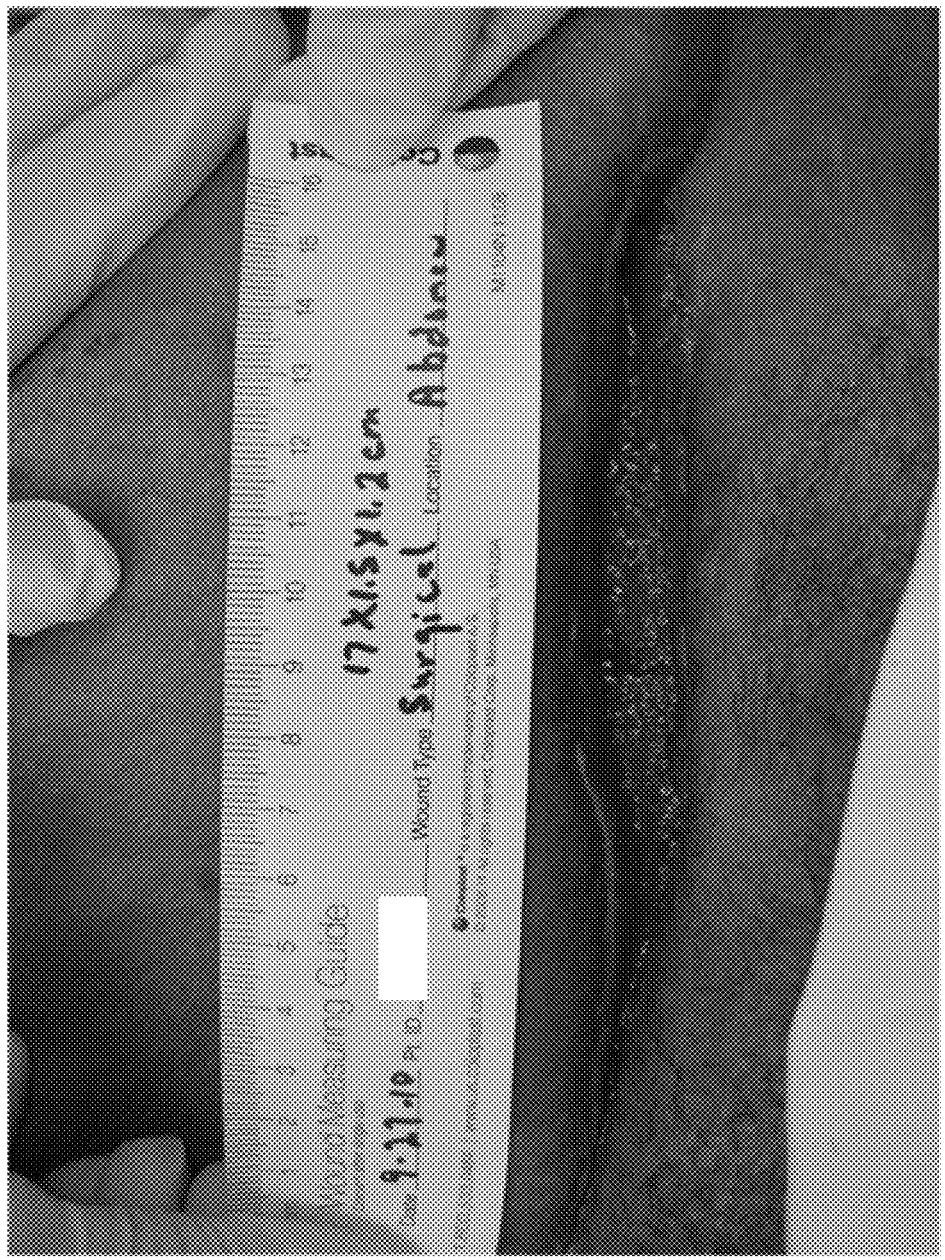
Figure 2E:
Figure 2F:
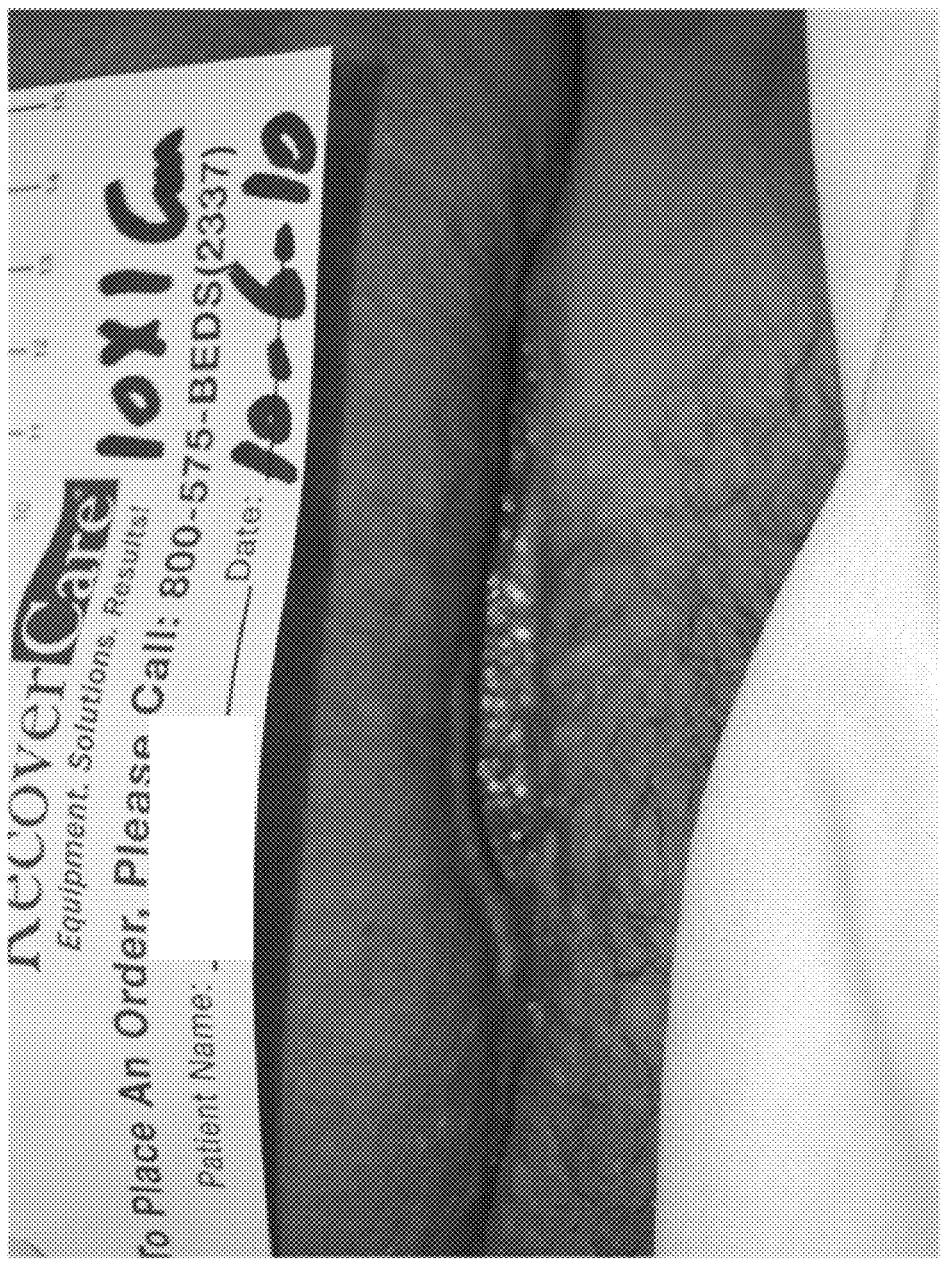

*Lawsonia inermis* extract, about 8.0% to about 13.0% w/w or w/v, was applied to a wound dressing and then the dressing was applied to the abdomen of a female patient following hysterectomy. The formulation was applied to the wound once a day, so that that the entire surface of the wound was covered with a thin layer of the formulation. FIG. 2A shows the wound at the beginning of treatment. FIG. 2B shows the wound at day 6 of treatment. FIG. 2C shows the wound at day 9 of treatment. FIG. 2D shows the wound at day 16 of treatment. FIG. 2E shows the wound at day 20 of treatment. FIG. 2F shows the wound at day 25 of treatment. Table 1 below represents that approximate dimensions of the wound during the treatment cycle, demonstrating the rapid healing of the wound. The wound healed in just over one month.

TABLE 1

| Treatment Day | Approximate Wound Dimensions (length × width × depth) in centimeters (cm) |
|---|---|
| 0 | 23 × 3.5 × 9.7 |
| 6 | 22 × 1.5 × 2.8 |

TABLE 1-continued

| Treatment Day | Approximate Wound Dimensions (length × width × depth) in centimeters (cm) |
|---|---|
| 9 | 19 × 2.0 × 2.0 |
| 16 | 17 × 1.5 × 1.2 |
| 20 | 12.5 × 1 |
| 25 | 10 × 1 |

Example 4

Clinical Study 1—Indigent Care Hospital Under County Ownership 19 patients were selected based on difficult diabetic acute wounds seen in an Orthopedic Surgery practice. The wounds ranged from wound dehiscence after trauma surgery to varied stages of diabetic foot wounds according to Wagner's Classification system. Only the most difficult wounds were selected for this treatment approach.

Lawsonia inermis extract 10% w/w or w/v, was prepared in the amount of 3 liters, retained for two weeks, and then delivered to the hospital for use in the clinical trial. Treatment consisted of daily topical application of the Lawsonia inermis extract with a spray to the surface of the wound, followed by the application of a Lawsonia inermis extract-soaked gauze dressing to the surface of the wound or packed into any deeper crevices. The wounds were monitored weekly. The results of the topical treatment are shown in FIG. 3 (Table 2).

Of the 19 patients included in the study, 10 were acute wounds that occurred as a result of infection or perioperative wound healing issues. They were of various sizes and depths, and were all treated with the Lawsonia inermis extract as described. They were followed for an average of 4 weeks or 25.9 days. Four patients were completely healed and the other six were at 82% of the original wound size when lost to follow up.

Of the 9 diabetic foot wounds, 5 were advanced Wagner 3 wounds with bone involvement prior to treatment. All were subjected to surgical debridement and removal of necrotic tissue prior to initiation of the Lawsonia inermis extract topical application. In the Wagner 3 group, the patients were followed for an average of 40 days and showed an average of 85% reduction in wound size over the period of follow up. The only patient with a Wagner 1 wound was healed in 5 days and the Wagner 2 patients took only an average of 20 days to show the same improvement as seen in the Wagner 3 group.

The only hospital supplies utilized were dry dressings and gauze or elastic wraps. The treatments were so successful that further operations and expensive antibiotic treatments were avoided. The results of this clinical study demonstrate that the Lawsonia inermis extract of the present invention promotes wound healing, is therapeutically effective in the topical treatment of wounds, and has suitable stability for extended use.

Example 5

Clinical Study 2—Institute for Advanced Wound Care

Twenty-five patients with an average age of 68, were recruited for the study. Three withdrew and 21 completed the study. The wounds had been present from one day to 88 weeks. The types of wounds ranged from spider bites and traumatic wounds to venous stasis ulcers.

Lawsonia inermis extract 10% w/w or w/v, was prepared in the amount of 7.2 liters, retained for two weeks, and then delivered to the Institute for use in the clinical trial. Treatment consisted of daily or weekly topical application of the Lawsonia inermis extract with a spray to the surface of the wound, followed by the application of a Lawsonia inermis extract-soaked gauze dressing to the surface of the wound.

There were 15 patients who healed within an average of 11 weeks; the shortest healing period was 2 weeks and the longest 48 weeks. Six others had excellent healing rates of 60%-83%. Application at daily and weekly dressing changes produced similar healing rates. It was also noted that the Lawsonia inermis extract was easy to apply and wound pain was reduced with treatment. Eleven of the patients were not healing with traditional therapies. These patients, unexpectedly, responded with good results. Seven of them healed completely. The results obtained with these patients are described below.

Patient A had a diabetic food ulcer that remained unhealed for 24 weeks when treated with Select Silver (wound dressing, Milliken Healthcare Products, LLC), Santyl® (collagenase, enzymatic debriding ointment, Smith & Nephew, Inc.), Prisma (wound dressing, Systagenix) and Clindamycin (antibiotic). When treated with the Lawsonia inermis extract, the wound healed completely in 18 weeks.

Patient B had a surgical site infection that after treatment for 36 weeks with Prisma, maggots, Drawtex (hydroconductive wound dressing, Beier Drawtex Healthcare), Amniox® (wound dressing, Amniox® Medical) and Vashe (wound cleansing solution, SteadMed Medical), still remained at a dramatically significant size of 32 cm×6 cm. When treated with the Lawsonia inermis extract, the wound healed completely in 48 weeks.

Patient C had a traumatic wound that after treatment for 8 weeks with Prisma, Lamisil (antifungal compound, terbinafine hydrochloride, Novartis), Regranex® (becaplermin gel, Smith & Nephew) and Promogran (wound dressing, Systagenix), still remained a significant size at 6 cm×3 cm. When treated with the Lawsonia inermis extract, the wound healed completely in 6 weeks.

Patient D had a traumatic wound that after treatment for 20 weeks with Prisma, compression and Regranex®, still failed to heal. When treated with the Lawsonia inermis extract, the wound healed to 75% in 24 weeks.

Patient E had a diabetic ulcer that after treatment for 88 weeks with Prisma, still failed to heal. When treated with the Lawsonia inermis extract, the wound healed to 72% in just 2.5 weeks.

Patient F had an abscess that after treatment for 14 weeks with Omnicide (topical antimicrobial gel, SteriWeb Medical) and Prisma, failed to heal. When treated with the Lawsonia inermis extract, the wound healed completely in just 10 weeks.

Patient G had a pressure ulcer that failed to heal after treatment for 60 weeks using Prisma and Mepilex® Ag (antimicrobial foam wound dressing, Mölnlycke Health Care). When treated with the Lawsonia inermis extract, the wound healed 60% in just 10 weeks.

Patient H had a traumatic wound that failed to heal after treatment for 2 weeks with Vaseline and Silvadene (silver sulfadiazine). When treated with the Lawsonia inermis extract, the wound healed completely in 2 weeks.

Patient I had a surgical site infection that failed to heal in 11 weeks after treatment with Prisma. When treated with the *Lawsonia inermis* extract, the wound healed 80% in just 19 weeks.

Patient J had a traumatic wound that failed to heal after treatment for 10 weeks with Prisma. When treated with the the *Lawsonia inermis* extract, the wound healed completely in 12 weeks.

Patient K had a surgical site infection that failed to heal after treatment for 23 weeks using steroid cream. When treated with the *Lawsonia inermis* extract, the wound healed completely in just 4 weeks.

The same 7.2 liter lot of the *Lawsonia inermis* extract was used for all patients in this study. Because of the remarkable efficacy of the *Lawsonia inermis* extract in promoting wound healing, the physician conducting this clinical study retained the extract for the next two years and continued to treat wound patients with it. The results of this study demonstrate the stability of the *Lawsonia inermis* extract of the present invention and its usefulness over long periods of time.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described without departing from the principle and scope of the invention as recited in the following claims.

I claim:

1. A topical formulation for promoting wound healing in the skin, comprising an aqueous extract of *Lawsonia inermis* leaves formed by placing 1% to 20%, w/w or w/v, of *Lawsonia inermis* leaves in water and allowing said water to extract the *Lawsonia inermis* leaves, wherein polymyxin B, clindamycin, and gentamycin are added to said water before or after forming said aqueous extract to render said aqueous extract stable for extended use in promoting wound healing in the skin following topical application of said aqueous extract to the skin and wherein said aqueous extract has no antibiotic activity after adding polymyxin B, clindamycin, and gentamycin to said aqueous extract.

2. The topical formulation of claim 1 wherein polymyxin B, clindamycin, and gentamycin are not present in said aqueous extract after said aqueous extract is formed.

3. The topical formulation of claim 1 wherein polymyxin B, clindamycin, and gentamycin are each added to said water in the amount of 0.001% to 0.003%, w/w or w/v.

4. The topical formulation of claim 1 wherein said aqueous extract is stable for extended use for at least 28 days.

5. A topical formulation for promoting wound healing in the skin, comprising an aqueous extract of *Lawsonia inermis* leaves formed by placing 1% to 20%, w/w or w/v, of *Lawsonia inermis* leaves in water and allowing said water to extract the *Lawsonia inermis* leaves, wherein polymyxin B, clindamycin, and gentamycin are added to said water before or after forming said aqueous extract to render said aqueous extract stable for extended use in promoting wound healing in the skin following topical application of said aqueous extract to the skin, wherein said aqueous extract has no antibiotic activity after adding polymyxin B, clindamycin, and gentamycin to said aqueous extract, and wherein said aqueous extract is stable for extended use for at least 28 days.

6. The topical formulation of claim 5 wherein polymyxin B, clindamycin, and gentamycin are not present in said aqueous extract after said aqueous extract is formed.

7. The topical formulation of claim 5 wherein polymyxin B, clindamycin, and gentamycin are each added to said water in the amount of 0.001% to 0.003%, w/w or w/v.

8. A method of forming an aqueous extract of *Lawsonia inermis* leaves, comprising placing 1% to 20%, w/w or w/v, of *Lawsonia inermis* leaves in water and allowing said water to extract the *Lawsonia inermis* leaves, wherein polymyxin B, clindamycin, and gentamycin are added to said water before or after forming said aqueous extract to render said aqueous extract stable for extended use in promoting wound healing in the skin by topical application of said aqueous extract to the skin and wherein said aqueous extract has no antibiotic activity after adding polymyxin B, clindamycin, and gentamycin to said aqueous extract.

9. The method of claim 8 wherein polymyxin B, clindamycin, and gentamycin are not present in said aqueous extract after said aqueous extract is formed.

10. The method of claim 8 wherein polymyxin B, clindamycin, and gentamycin are each added to said water in the amount of 0.001% to 0.003%, w/w or w/v.

11. The method of claim 8 wherein said aqueous extract is stable for extended use for at least 28 days.

12. A method of forming an aqueous extract of *Lawsonia inermis* leaves, comprising placing 1% to 20%, w/w or w/v, of *Lawsonia inermis* leaves in water and allowing said water to extract the *Lawsonia Inermis* leaves, wherein polymyxin B, clindamycin, and gentamycin are added to said water before or after forming said aqueous extract to render said aqueous extract stable for extended use in promoting wound healing in the skin by topical application of said aqueous extract to the skin, wherein said aqueous extract has no antibiotic activity after adding polymyxin B, clindamycin, and gentamycin to said aqueous extract, and wherein said aqueous extract is stable for the extended use for at least 28 days.

13. The method of claim 12 wherein polymyxin B, clindamycin, and gentamycin are not present in said aqueous extract after said aqueous extract is formed.

14. The method of claim 13 wherein polymyxin B, clindamycin, and gentamycin are each added to said water in the amount of 0.001% to 0.003%, w/w or w/v.

* * * * *